United States Patent [19]

Conradie et al.

[11] Patent Number: 5,399,190
[45] Date of Patent: Mar. 21, 1995

[54] WOOD PRESERVATIVES

[75] Inventors: Wilhelm E. Conradie, Pretoria, South Africa; Andrew J. Pendlebury, Delft, Netherlands; Antonio Pizzi, Irene; Denise Conradie, Verwoerdburg, both of South Africa

[73] Assignees: Shell South Africa (Pty.) Ltd., Johannesburg; CSIR, Pretoria, both of South Africa; Shell Research Ltd., London, United Kingdom

[21] Appl. No.: 989,008
[22] PCT Filed: Sep. 2, 1991
[86] PCT No.: PCT/GB91/01480
  § 371 Date: May 3, 1993
  § 102(e) Date: May 3, 1993
[87] PCT Pub. No.: WO92/04166
  PCT Pub. Date: Mar. 19, 1992

[30] Foreign Application Priority Data

Sep. 3, 1990 [ZA] South Africa .................. 90/7003

[51] Int. Cl.⁶ .................. A01N 3/00; A01N 25/00
[52] U.S. Cl. .................. 106/18; 106/18.3; 106/18.36; 252/380; 252/384; 424/405; 514/492; 514/493; 514/494; 514/498; 514/499; 514/500; 514/501; 514/502; 514/503; 514/504; 514/505; 514/558
[58] Field of Search .......... 106/18, 18.36, 18.3; 252/380, 384; 514/492, 493, 494, 498, 499, 500, 501, 502, 503, 504, 505, 558; 424/405

[56] References Cited

U.S. PATENT DOCUMENTS

| | | | |
|---|---|---|---|
| 2,561,380 | 7/1951 | Kalberg | 106/18 |
| 2,951,789 | 9/1960 | McCants | 514/494 |
| 4,234,665 | 11/1980 | Johnston | 106/18.32 |
| 4,532,161 | 7/1985 | Collins et al. | 106/18 |
| 4,612,255 | 9/1986 | Hein | 106/18.29 |
| 4,649,065 | 3/1987 | Hein et al. | 106/18 |
| 4,786,326 | 11/1988 | Grove | 106/18 |
| 5,104,654 | 4/1992 | Baker et al. | 106/18 |

FOREIGN PATENT DOCUMENTS 2121285 12/1983 United Kingdom.
2168394 6/1986 United Kingdom.

*Primary Examiner*—Anthony Green
*Attorney, Agent, or Firm*—Kenyon & Kenyon

[57] ABSTRACT

A wood preservative composition including a mixture of two or more metallic soaps of long chain unsaturated fatty acids, which soaps have a metallic component selected from the group consisting of copper, zinc, chromium, iron, antimony, tin, cobalt, nickel, arsenic, boron, lead, magnesium, potassium and sodium, and a fatty acid component selected from two or more of the group consisting of oleic acid, linoleic acid, and linolenic acid, the composition being such that the ratio by mass of metallic soap of oleic acid:metallic soap of linoleic acid:metallic soap of linolenic acid is about 20–29:-15–70:0–47.

10 Claims, No Drawings

WOOD PRESERVATIVES

This invention relates to wood preservatives. More specifically this invention relates to a wood preservative suitable for use in protecting wood against attack by microorganisms and insects, more particularly fungi and termites.

Various wood preservatives which have been in use for many years have in recent times been identified as environmentally harmful. Some of these have now been withdrawn from the market in certain countries and it is expected that the increasing environmental awareness will lead to the withdrawal of more of these products in a growing number of countries. Included amongst these preservatives are the products known as pentachlorophenol [PCP], copper chromium arsenate [CCA], creosote and tributyl tin oxide [TBTo]. The search for replacement products which have no, or a smaller, environmental impact and which are yet effective in protecting wood against insect and microorganism attack, particularly against termite and fungal attack, is continuing unabated by many research companies in the world.

It is an object of the present invention to provide a wood preservative composition which it is believed would fulfill these needs.

It has been reported in the literature that the metal soaps of naturally occurring organic acids such as oleic, stearic, and tall oil acids has been suggested as preservatives to protect cellulose materials against fungal attack but has been found to be inferior to the metal naphthenates. [See for example "The Development and use of Naphthenates for Timber Preservation", by R A Bulman, Record British Wood Preservating Association (1955) p. 36 at 40]. The use of copper tallate, i.e. the copper soap of tall oil acid which comprises a mixture of fatty acids [oleic, linoleic, palmitic and stearic] and rosin acid [abietic acid] has been suggested as a pesticide in the preservation of cellulosic materials such as wood. [See U.S. Pat. No. 2,584,041].

The present invention relates to a wood preservative composition comprising metal soaps of a mixture of naturally occurring fatty acids in a specific compositional ratio range which composition has been shown to be a superior preservative to termite and fungal attack on wood when compared to the metal naphthenates. By implication the composition is hence also superior to the individual metallic soaps of fatty acids referred to above and the tall oil acid metallic soap mixture.

According to the present invention there is provided a wood preservative composition comprising a mixture of two or more metallic soaps of long chain unsaturated fatty acids, the metallic component of the soaps being selected from the group consisting of copper, zinc, chromium, iron, antimony, tin, cobalt, nickel, arsenic, boron, lead, magnesium, potassium and sodium and the fatty acid component comprising at least two of the group consisting of oleic acid, linoleic acid, and linolenic acid such that the ratio by mass of the metallic soaps of oleic acid: linoleic acid: linolenic acid is about 20–29:- 15–70:0–47. The iodine value of the metallic soap mixture is preferably between 125 and 180.

The mixture may in addition also include saturated fatty acid metallic soaps such as a metallic soap derived from stearic acid and palmitic acid, and if present, the stearic acid and palmitic acid metal soaps may be present in a quantity constituting between 1.0 and 6.5 and between 5 and 11.5 parts by mass respectively.

In a preferred form of the invention the mass ratio of the fatty acid soaps in the preservative composition falls preferably in the following ranges:

Stearic acid soap:oleic acid soap:linoleic acid soap:- linolenic acid soap:palmitic acid soap of about 1.0–6.5:24.5–28.6:49.8–70.0:0–0.4:5.0–11.5.

Most preferably, however, the ratio by mass of the stearic acid soap:oleic acid soap:linoleic acid soap:linolenic acid soap:palmitic acid soap is about 4.8:26.6: 54.8:0.1:8.5.

In the preferred form of the present invention the metallic component of the metal soaps is copper $[Cu^{++}]$. The metal soaps forming the preservative composition of the present invention may be prepared as described in our co-pending International Patent Application No. PCT/GB91/01481, Publication No. WO92/04167 entitled "METHOD OF PRODUCING METAL SOAPS" incorporated herein by reference.

According to a further aspect of the present invention the wood preservative composition may further include any known insecticide and/or fungicide.

In the preferred form of this aspect of the present invention the additional insecticide is preferably a synthetic pyrethroid, most preferably cypermethrin.

The wood preservative composition may further comprise a carrier medium which is preferably xylene. The metallic soap composition is preferably made up to contain at least 5% copper metal by mass in xylene.

The metal soap solution so obtained may be used as such as a wood preservative or diluted in a suitable solvent carrier for application in any convenient manner to timber to be treated. The solution may further be modified to render it water dispersible by formulation of an emulsifiable concentrate or microemulsion concentrate by using one or more appropriate surface active agents as is known in the trade.

Without thereby limiting the scope of the present invention a preferred embodiment will now be described with reference to the accompanying examples illustrating the efficacy of the product.

EXAMPLE 1

Biological Performance of Fatty Acid Soaps of Copper against Termites

A Preparation of Preservative Compositions and Controls

[i] CuLin1

A mixture of fatty acid soaps produced from sunflower oil and copper sulphate in the manner described in our co-pending South African patent application entitled "METHOD OF PRODUCING METAL SOAPS" [which is incorporated herein by reference] was prepared and the metallic soap dissolved in Xylene to a final concentration of at least 5% [m/m] copper metal. Since the predominant constituent of the mixture is copper linoleate, the composition was coded CuLin1. It will however be understood that since the sunflower oil used as starting material also contains, albeit in derivative form as a triglyceride oil, other fatty acids including stearic acid, oleic acid, linoleic acid and palmitic acid, the copper soaps of these acids are also present in CuLin1. The exact composition of CuLin1 was not determined. However since the typical fatty acid composition of sunflower oil is as follows:

| | |
|---|---|
| stearic acid | 2.2% |
| oleic acid | 25.1% |
| linoleic acid | 66.2% |
| palmitic acid | 5.6% |

[*Biology Data Book* by H. J. Hartwood and R.P. Geyer, 1964] and since it is expected that the conversion of such acids to the corresponding soaps is complete, it is expected that the corresponding soaps are present in CuLin1 in approximately the same ratio.

[ii] Cypermethrin

A commercially available composition containing cypermethrin as active ingredient [Devatern TM as marketed by Shell Chemicals (Pty.) Limited] was used according to the manufacturer's specifications and instructions.

[iii] CuLin1+Cypermethrin

A mixture of CuLin1 as described in [i] above and cypermethrin as identified in [ii] above was prepared to obtain a combination product.

[iv] CCA

An industrial standard wood preservative containing copper chromium arsenate as active ingredients was prepared from AR Chemicals in accordance with S.A.B.S. specification 673 (1987) and was used in accordance with internationally recognized commercial practice.

[v] Sunflower Oil

A solution of commercially available sunflower oil in xylene was prepared for use as a control.

[vi] $CUSO_4.5H_2O$

An aqueous solution of $CUSO_4$ was prepared.

B. Treatment of Test Stakes and Experimental Conditions

*Pinus patula* sapwood stakes measuring $100 \times 10 \times 10$ mm were impregnated with the preservative and control formulations by the process known in the trade as the full-cell process to the target retentions specified in Table 1 below. Five replicates per preservative per retention level were used and in respect of the test preservatives the samples were duplicated to provide a set of aged and a set of unaged samples. The aging of the aged samples was carried out by placing the treated stakes in water for one day and in an oven at 60° C. for 1 day alternating for a period of 10 days.

The stakes were randomly knocked into the ground at the test site to half their lengths and were visually graded for termite attack after the time lapses set out in Table 1. The percentage grade of attack was determined by the method described by Jansen et. al. in CSIR Internal Report, FOR-I4, May 1990.

In terms of this evaluation procedure a 100% grade of attack is reached when a test stake is decayed to half its cross-sectional area. Rasping of the surface such as would be the result of mere sampling of the test stake is regarded in terms of the method as amounting to 3% attack.

The test was started during July 1989 and is still ongoing. The results available as at the date hereof are set out in Table 1.

TABLE 1

BIOLOGICAL PERFORMANCE OF CuLin1 AND CYPERMETHRIN AGAINST TERMITES

Grade of attack (%) after x months exposure

| Preservatives | Retention (Kg a.i./m³) | Retention (Kg Cu. a.e./m³) | 1 Month Aged | 1 Month Unaged | 6 Months Aged | 6 Months Unaged | 9 Months Aged | 9 Months Unaged | 15 Months Aged | 15 Months Unaged | 18 Months Aged | 18 Months Unaged | 20 Months Aged | 20 Months Unaged | 22 Months Aged | 22 Months Unaged |
|---|---|---|---|---|---|---|---|---|---|---|---|---|---|---|---|---|
| CuLin1 | 5 | 0.50 | 0 | 0 | 2.4 | 3.6 | 8.8 | 3.6 | 24.8 | 62.4 | 24.8 | 62.4 | 24.8 | 62.4 | 24.8 | 62.4 |
|  | 10 | 1.00 | 0 | 0 | 0 | 1.2 | 1.2 | 1.2 | 10.4 | 2.4 | 10.4 | 2.4 | 11.6 | 7.6 | 11.6 | 7.6 |
|  | 15 | 1.50 | 0 | 0 | 0 | 0 | 0 | 1.2 | 13.2 | 5.2 | 13.2 | 5.2 | 15.6 | 5.2 | 15.6 | 5.2 |
|  | 20 | 2.00 | 0 | 0 | 0 | 1.2 | 0 | 2.4 | 1.2 | 2.4 | 1.2 | 2.4 | 2.4 | 3.6 | 2.4 | 3.6 |
| Cypermethrin (OS) | 0.05 | — | 0 | 0 | 0 | 0 | 1.2 | 0 | 1.2 | 17.2 | 17.2 | 26.4 | 21.2 | 26.4 | 21.2 | 26.4 |
|  | 0.10 | — | 0 | 0 | 1.2 | 0 | 13.2 | 17.2 | 13.2 | 1.2 | 13.2 | 1.2 | 25.2 | 1.2 | 25.2 | 1.2 |
|  | 0.15 | — | 0 | 0 | 4.0 | 0 | 4.0 | 0 | 9.2 | 0 | 13.2 | 8.0 | 14.4 | 12.0 | 14.4 | 12.0 |
|  | 0.20 | — | 0 | 0 | 0 | 0 | 0 | 0 | 0 | 0 | 0 | 0 | 4.8 | 3.6 | 4.8 | 3.6 |
| CuLin1 plus Cypermethrin (OS) | 5.050 | 0.50 | 0 | 0 | 0 | 0 | 0 | 0 | 1.2 | 0 | 2.4 | 0 | 3.6 | 1.2 | 3.6 | 1.2 |
|  | 7.575 | 0.75 | 0 | 0 | 0 | 0 | 0 | 0 | 1.2 | 0 | 1.2 | 0 | 2.4 | 0 | 2.4 | 0 |
|  | 10.100 | 1.00 | 0 | 0 | 0 | 0 | 0 | 0 | 0 | 0 | 0 | 0 | 2.4 | 0 | 2.4 | 0 |
|  | 12.625 | 1.25 | 0 | 0 | 0 | 0 | 0 | 0 | 0 | 0 | 0 | 0 | 2.4 | 0 | 2.4 | 0 |
|  | 15.150 | 1.50 | 0 | 0 | 0 | 0 | 0 | 0 | 1.2 | 1.2 | 1.2 | 1.2 | 1.2 | 1.2 | 1.2 | 1.2 |
| CCA Type C Salt | 5 | 0.45 | 0 | 0 | 0 | 0 | 0 | 0 | 4.0 | 0 | 4.0 | 0 | 6.4 | 3.6 | 7.6 | 3.6 |
|  | 10 | 0.90 | 0 | 0 | 0 | 0 | 0 | 0 | 0 | 0 | 0 | 0 | 1.2 | 2.4 | 1.2 | 2.4 |
|  | 15 | 1.35 | 0 | 0 | 0 | 0 | 0 | 1.2 | 0 | 2.4 | 0 | 2.4 | 1.2 | 3.6 | 1.2 | 3.6 |
| Controls: |  |  |  |  |  |  |  |  |  |  |  |  |  |  |  |  |
| Sunflower Oil | 5 | — | — | 1.2 | — | 88.0 | — | 88.0 | — | 100.0 | — | 100.0 | — | 100.0 | — | 100.0 |
|  | 10 | — | — | 0 | — | 92.0 | — | 100.0 | — | 100.0 | — | 100.0 | — | 100.0 | — | 100.0 |
|  | 15 | — | — | 0 | — | 64.0 | — | 80.0 | — | 100.0 | — | 100.0 | — | 100.0 | — | 100.0 |
|  | 20 | — | — | 0 | — | 48.0 | — | 84.0 | — | 80.0 | — | 80.0 | — | 80.0 | — | 80.0 |
| CuSO$_4$.5H$_2$O | 5 | 1.27 | — | 0 | — | 88.0 | — | 100.0 | — | 100.0 | — | 100.0 | — | 100.0 | — | 100.0 |
|  | 10 | 2.54 | — | 0 | — | 52.0 | — | 36.0 | — | 80.0 | — | 92.0 | — | 92.0 | — | 92.0 |
|  | 15 | 3.82 | — | 0 | — | 25.2 | — | 68.0 | — | 68.0 | — | 68.0 | — | 68.0 | — | 68.0 |
|  | 20 | 5.09 | — | 0 | — | 24.0 | — | 32.0 | — | 60.0 | — | 60.0 | — | 64.0 | — | 64.0 |
| Untreated Controls | — | — | — | 0.6 | — | 80.0 | — | 94.0 | — | 94.0 | — | 94.0 | — | 96.0 | — | 96.0 |

— = not performed; a.i. = active ingredient; a.e. = active element

Discussion

From the aforegoing results it is clear that significant failures of the untreated [control] test stakes [more than 30% attack] started to set in between only about 1 and 6 months after exposure to termites and that virtually complete failure [more than 80% attack] occurred in less than one year except in the case of the higher retention levels of $CuSO_4$.

In contrast, save for the lowest retention levels of the CuLin1 and cypermethrin, the stakes treated with test preservatives were at most only slightly attacked even after 22 months. It is pointed out that percentages of less than 3% represent mere rasping or sampling of only some of the replicate samples.

What is regarded as highly significant is that the combination of CuLin1 and cypermethrin appears to create a synergistic or potentiating effect in that stakes treated with the combination of these products show significantly better resistance to termite attack compared to stakes treated with those products individually to the same retention levels.

EXAMPLE 2

Biological Performance of Wood Preservatives against Fungi

A. Preservative Compositions and Controls

The same compositions as described in Example 1 were used in this Example.

B. Treatment of Test Blocks and Experimental Conditions

*Pinus patula* blocks measuring 100×10×10 mm were treated by the method described in Example 1 to achieve retention levels of the test compositions as set out in Table 2 below.

The blocks were randomly placed to half their lengths in unsterile soil samples in trays which soil samples contain an unidentified fungal population known to be active against timber. The test trays were kept at about 27°–28° C. at about 80% humidity to enhance fungal activity.

The same visual evaluation method referred to in Example 1 was used to evaluate % grade of attack.

The results are set out in Table 2.

TABLE 2

BIOLOGICAL PERFORMANCE OF COPPER LINOLEATE AND CYPERMETHRIN AGAINST FUNGI

| Preservatives | Retention (Kg a.i./m³) | Retention (Kg Cu. a.e./m³) | 4 Month Aged | 4 Month Un-aged | 6 Months Aged | 6 Months Un-aged | 9 Months Aged | 9 Months Un-aged | 11 Months Aged | 11 Months Un-aged | 18 Months Aged | 18 Months Un-aged | 22 Months Aged | 22 Months Un-aged |
|---|---|---|---|---|---|---|---|---|---|---|---|---|---|---|
| CuLin1 | 5 | 0.50 | 0 | 0 | 0 | 0 | 0 | 0 | 0 | 1.2 | 2.4 | 8.0 | 6.4 | 15.6 |
|  | 10 | 1.00 | 0 | 0 | 0 | 0 | 0 | 0 | 0 | 0 | 3.6 | 9.2 | 7.6 | 18.4 |
|  | 15 | 1.50 | 0 | 0 | 0 | 0 | 0 | 0 | 0 | 0 | 2.4 | 1.2 | 3.6 | 3.6 |
|  | 20 | 2.00 | 0 | 0 | 0 | 0 | 0 | 0 | 0 | 0 | 2.4 | 2.4 | 3.6 | 4.8 |
| Cypermethrin (OS) | 0.05 | — | 0 | 0 | 0 | 0 | 33.2 | 8.0 | 52.0 | 60.0 | 84.0 | 72.0 | 100.0 | 100.0 |
|  | 0.10 | — | 0 | 0 | 0 | 0 | 13.2 | 29.2 | 45.2 | 64.0 | 68.0 | 92.0 | 88.0 | 100.0 |
|  | 0.15 | — | 0 | 0 | 0 | 0 | 28.0 | 28.0 | 80.0 | 56.0 | 92.0 | 60.0 | 100.0 | 100.0 |
|  | 0.20 | — | 0 | 0 | 0 | 0 | 18.4 | 5.2 | 16.4 | 53.2 | 68.0 | 64.0 | 100.0 | 88.0 |
| CuLin1 plus Cypermethrin (OS) | 5.050 | 0.50 | 0 | 0 | 0 | 0 | 0 | 0 | 0 | 3.6 | 4.0 | 4.8 | 15.6 | 32.0 |
|  | 7.575 | 0.75 | 0 | 0 | 0 | 0 | 0 | 0 | 0 | 0 | 2.4 | 3.6 | 4.8 | 11.6 |
|  | 10.100 | 1.00 | 0 | 0 | 0 | 0 | 0 | 0 | 0 | 0 | 2.4 | 2.4 | 2.4 | 6.0 |
|  | 12.625 | 1.25 | 0 | 0 | 0 | 0 | 0 | 0 | 1.2 | 0 | 4.8 | 2.4 | 6.0 | 9.2 |
|  | 15.150 | 1.50 | 0 | 0 | 0 | 0 | 0 | 0 | 0 | 0 | 6.4 | 2.4 | 6.0 | 2.4 |
| CCA Type C Salt | 5 | 0.45 | 0 | 0 | 0 | 0 | 0 | 0 | 0 | 1.2 | 6.4 | 4.8 | 14.4 | 14.4 |
|  | 10 | 0.90 | 0 | 0 | 0 | 0 | 0 | 0 | 0 | 0 | 4.8 | 1.2 | 4.8 | 3.6 |
|  | 15 | 1.35 | 0 | 0 | 0 | 0 | 0 | 0 | 0 | 0 | 1.2 | 2.4 | 2.4 | 2.4 |
| Controls: |  |  |  |  |  |  |  |  |  |  |  |  |  |  |
| Sunflower Oil | 5 | — | — | 0 | — | 22.4 | — | 64.0 | — | 76.0 | — | 92.0 | — | 100.0 |
|  | 10 | — | — | 0 | — | 1.2 | — | 45.2 | — | 61.2 | — | 76.0 | — | 88.0 |
|  | 15 | — | — | 0 | — | 20.0 | — | 10.4 | — | 60.0 | — | 60.0 | — | 92.0 |
|  | 20 | — | — | 0 | — | 7.6 | — | 49.2 | — | 88.0 | — | 100.0 | — | 100.0 |
| $CuSO_4.5H_2O$ | 5 | 1.27 | — | 0 | — | 5.2 | — | 84.0 | — | 84.0 | — | 100.0 | — | 100.0 |
|  | 10 | 2.54 | — | 0 | — | 4.0 | — | 31.6 | — | 46.4 | — | 76.0 | — | 88.0 |
|  | 15 | 3.82 | — | 0 | — | 0 | — | 31.6 | — | 49.2 | — | 72.0 | — | 88.0 |
|  | 20 | 5.09 | — | 0 | — | 0 | — | 10.4 | — | 24.0 | — | 60.0 | — | 76.0 |
| Untreated Controls | — | — | — | 0 | — | 3.6 | — | 68.6 | — | 70.0 | — | 94.0 | — | 100.0 |

— = not performed; a.i. = active ingredient; a.e. = active element

Discussion

From the aforegoing results it is clear that all the treatments performed some protective role against fungal attack relative to the untreated samples. However, it should be borne in mind that even sunflower oil and $CuSO_4$ on their own also showed some protective activity. In contrast cypermethrin on its own had a much lower protective efficacy than any of the other treatments except for sunflower oil.

What is highly significant though is that CuLin1 and the combination of CuLin1 and cypermethrin appear to be as effective as CCA on the basis of an 22 months test.

Further experiments to determine the threshold activity of CuLin1 and CuLin1 +cypermethrin are in progress.

EXAMPLE 3

Biological Performance of Alternative CuLin Preparation on Termites and Fungi

A. Preparation of Preservative Compositions and Controls

[i] CuLin2

An alternative copper linoleate preparation was prepared in accordance with the method disclosed in our co-pending patent application entitled "METHOD OF PRODUCING METAL SOAPS" [incorporated herein by reference] but using the Sunflower Oil fraction known as Sunflower Acid Oil ["Prifac 033X" ex Silicate & Chemical Industries, Durban, the analysis of which is given below] as starting material. The resulting fatty acid soap mixture was coded CuLin2.

The composition of CuLin2 was determined by GC-analysis.

A specific amount [10 g] of CuLin2 was weighed off and heated to boiling point in combination with 50–100 ml of 6N HCl [hydrochloric acid].

The solution was filtered into a separating funnel and then washed [3 times] with a 2 to 1 solution of hexane and ether. The hexane/ether phase contained all the free fatty acids resulting from the hydrolysis while the water-phase contained the $CuCl_2$.

| Fatty Acid Profile [g/100 g fatty acids] | | |
|---|---|---|
| | CuLin2 [1 sample] | Sunflower Acid Oil [Average from 20 batches given by SCI] |
| C14: Myristic acid | 0.31 | 0.3 |
| C16:0 Palmitic acid | 6.55 | 8.5 |
| C18:0 Stearic acid | 4.49 | 4.8 |
| C18:1 Oleic acid | 25.17 | 26.6 |
| C18:2 Linoleic | 58.10 | 54.8 |
| C18:3 Linolenic acid | 0.10 | 0.1 |
| C20:0 Arachidic acid | 0.24 | — |
| C20:1 | 0.20 | — |
| C20:2 | 0.22 | — |
| C22:0 Behenic acid | 0.46 | — |

The results obtained in this profile show that the conversion of the acid to the corresponding soaps was substantially complete.

Another analytical process was also carried out whereby the CuLin was first washed with hexane to remove any unreacted free fatty acids. The washed CuLin was then also heated to boiling point in combination with 50–100 ml 6N HCl with the rest of the process being repeated as before. The same GC fatty acid profile as that detailed above was obtained.

[ii] CuLin2 +Cypermethrin

In the manner described above in Example 1 a combination product containing CuLin2 and cypermethrin was prepared.

Comparative Formulations and Controls

In addition to the other test formulations referred to above the following additional preservative formulations were used in accordance with the manufacturer's recommendations, namely:

[iii] Pentachlorophenol [PCP] obtained from Chemico (Pty.) Ltd., Durban.

[iv] Creosote obtained from Suprachem (Pty.) Ltd., Pretoria.

[v] Copper naphthenate obtained from C. G. Smith Chemicals, Durban.

[v] Zinc naphthenate obtained from C. G. Smith Chemicals, Durban.

A test program, similar to the program described in Examples 1 and 2 above and commencing during January 1990 was conducted and the same evaluation system was followed. In this program 10 replicates were used for each formulation. The samples were not aged.

TABLE 3

BIOLOGICAL PERFORMANCE OF COPPER LINOLEATE IN COMPARISON WITH OTHER WOOD PRESERVATIVES

| Preservatives | Retention (kg a.i./m$^3$) | Retention (kg Cu. a.e./m$^3$) | 1.5 Month Termites | 1.5 Month Fungi | 5 Months Termites | 5 Months Fungi | 9 Months Termites | 9 Months Fungi | 16 Months Termites | 16 Months Fungi |
|---|---|---|---|---|---|---|---|---|---|---|
| CuLin2 | 10 | 1.00 | 8.0 | — | 8.0 | 1.2 | 8.0 | 8.0 | 13.2 | 41.2 |
|  | 15 | 1.50 | 0 | — | 0 | 0 | 0 | 0 | 1.2 | 46.4 |
|  | 20 | 2.00 | 0 | — | 1.2 | 0 | 1.2 | 0 | 1.2 | 22.4 |
| CuLin2 plus | 7.575 | 0.75 | 0 | — | 0 | 0 | 0 | 2.4 | 1.2 | 69.2 |
| Cypermethrin | 10.1 | 1.00 | 0 | — | 0 | 0 | 0 | 1.2 | 1.2 | 40.0 |
| (OS) | 15.15 | 1.50 | 0 | — | 0 | 0 | 0 | 0 | 0 | 16.0 |
| Cypermethrin | 0.1 | — | 0 | — | 0 | 21.2 | 0 | 22.4 | 40.0 | 60.0 |
| (OS) | 0.15 | — | 0 | — | 0 | 23.6 | 0 | 30.4 | 44.0 | 100.0 |
|  | 0.2 | — | 0 | — | 0 | 61.2 | 0 | 81.2 | 29.2 | 100.0 |
| CCA Type C | 5 | 0.45 | 0 | — | 9.2 | 1.2 | 9.2 | 21.2 | 14.4 | 68.0 |
| Salt | 10 | 0.90 | 0 | — | 0 | 0 | 0 | 1.2 | 0 | 34.4 |
|  | 15 | 1.35 | 0 | — | 1.2 | 0 | 1.2 | 0 | 1.2 | 3.6 |
| PCP (OS) | 5 | — | 0 | — | 0 | 1.2 | 2.4 | 15.6 | 9.2 | 96.0 |
|  | 10 | — | 0 | — | 1.2 | 4.0 | 1.2 | 4.0 | 20.0 | 52.0 |
|  | 15 | — | 0 | — | 0 | 0 | 0 | 0 | 0 | 28.0 |
| Creosote | 33 | — | 0 | — | 2.4 | 4.0 | 2.4 | 9.2 | 5.2 | 56.0 |
|  | 67 | — | 0 | — | 4.0 | 0 | 4.0 | 2.4 | 5.2 | 68.0 |
|  | 100 | — | 0 | — | 0 | 0 | 0 | 0 | 1.2 | 68.0 |
| Copper | — | 1.00 | 0 | — | 1.2 | 1.2 | 16.0 | 14.4 | 17.2 | 100.0 |
| naphthenate | — | 1.50 | 0 | — | 1.2 | 0 | 1.2 | 1.2 | 2.4 | 81.2 |
| (OS) | — | 2.00 | 0 | — | 0 | 0 | 0 | 1.2 | 0 | 68.0 |
| Zinc | — | 1.00* | 0 | — | 40.0 | 2.4 | 61.2 | 9.2 | 80.0 | 80.0 |
| naphthenate | — | 1.50* | 0 | — | 34.4 | 5.2 | 34.4 | 41.2 | 41.2 | 100.0 |
| (OS) | — | 2.00* | 0 | — | 22.4 | 4.0 | 22.4 | 52.0 | 57.2 | 92.0 |
| Untreated Controls | — | — | 52.0 | — | 100.0 | 48.4 | 100.0 | 84.0 | 100.0 | 100.0 |

*Retention [kg Zn a.e./m$^3$]
— = not performed; a.i. = active ingredient; a.e. = active element Discussion From the results given it is clear that CuLin2 compares well with commercially available wood preservatives. It is particularly significant to note that at the same retention rates CuLin2 performed much better than copper naphthenate particularly over the 12 month period.

waters of the highest retention of each preservative were analyzed. All the solutions containing Cu, Cr, As and Zn were analyzed by AA-spectrophotometry. The results obtained are shown in Table 4.

TABLE 4

LEACHING TEST RESULTS

| TREATMENT | RETENTION kg a.e./m³* AVERAGE PRESERVATIVE RETENTION | TOTAL ELEMENTS mg/l | | | | PRESERVATIVE/ELEMENTS LEACHED | | | | | | | |
|---|---|---|---|---|---|---|---|---|---|---|---|---|---|
| | | | | | | mg/l | | | | % | | | |
| | | Cu | Cr | As | Zn | Cu | Cr | As | Zn | Cu | Cr | As | Zn |
| Cold water leaching | | | | | | | | | | | | | |
| CuLin2 | 1.43 | 190.4 | — | — | — | 4.65 | — | — | — | 2.44 | — | — | — |
| CuLin2 + Cypermethrin* | 1.53 + 0.15 | 204.1 | — | — | — | 4.50 | — | — | — | 2.21 | — | — | — |
| CuLin EC | 1.37 | 182.9 | — | — | — | 20.70 | — | — | — | 11.32 | — | — | — |
| CuLin EC + Cypermethrin** | 1.54 + 0.5 | 205.3 | — | — | — | 25.80 | — | — | — | 12.57 | — | — | — |
| CCA Type C salt | 1.23 | 163.6 | 266.4 | 235.6 | — | 1.80 | 0.60 | 5.20 | — | 1.70 | 0.25 | 2.21 | — |
| Copper naphthenate | 1.52 | 203.2 | — | — | — | 11.45 | — | — | — | 5.64 | — | — | — |
| Zinc naphthenate | 1.66 | — | — | — | 221.1 | — | — | — | 21.50 | — | — | — | 9.72 |
| Water Soxhlet leaching | | | | | | | | | | | | | |
| CuLin2 | 1.42 | 189.6 | — | — | — | 11.40 | — | — | — | 6.01 | — | — | — |
| CuLin2 + Cypermethrin* | 1.45 + 0.15 | 193.5 | — | — | — | 13.30 | — | — | — | 6.87 | — | — | — |
| CuLin EC | 1.36 | 181.7 | — | — | — | 25.10 | — | — | — | 13.81 | — | — | — |
| CuLin EC + Cypermethrin** | 1.62 + 0.16 | 216.0 | — | — | — | 26.90 | — | — | — | 12.45 | — | — | — |
| CCA Type C salt | 1.44 | 191.8 | 312.3 | 276.2 | — | 11.60 | 0.80 | 12.10 | — | 6.05 | 0.26 | 4.38 | — |
| Copper naphthenate | 1.56 | 208.3 | — | — | — | 24.70 | — | — | — | 11.86 | — | — | — |
| Zinc naphthenate | 1.56 | — | — | — | 208.3 | — | — | — | 25.80 | — | — | — | 12.39 |

*a.e. = active element [Cu, Zn]; — = not performed
**retention based on total product Again a synergistic effect between cypermethrin and CuLin2 with regard to anti-termite effect is suggested by the results.

The following examples illustrate the physical properties of the CuLin2 preservative composition.

EXAMPLE 4

Leaching tests in respect of CuLin2

*Pinus patula* sapwood blocks of dimensions 20×20×10 mm were impregnated with the following preservatives.

[a] CuLin2:target retention 1.5 kg Cu a.e./m³.
[b] CuLin2 +Cypermethrin:target retention 1.5 kg Cu a.e./m³ plus 0.15 kg Cypermethrin/m³.
[c] CuLin EC:target retention 1.5 kg Cu a.e./m³.
[d] CuLin EC +Cypermethrin EC target retention 1.5 kg Cu a.e./m³ plus 0.15 kg Cypermethrin EC/m³.
[e] CAA Type C salt:target retention 1.35 kg Cu a.e./m³.
[f] Cu Naphthenate:target retention 1.5 kg Cu a.e./m³.
[g] Zn Naphthenate:target retention 1.5 kg Zn a.e./m³.

The preparation of CuLin EC and CuLin EC + Cypermethrin EC is described in Example 8 below.

The samples were conditioned to ±8% moisture content and were then treated by the full-cell process with the above-mentioned preservatives to the target retentions specified. After treatment the samples were leached by two different procedures. Ten specimens for each case were leached by water soxhlet at reflux for six hours and ten specimens for each case were leached in 300 ml cold distilled water for five days. The leached Discussion The resistance to leaching of any preservative compound is an extremely important factor in determining its ability to provide effective protection to timber under exterior service conditions, e.g. although boron is an effective insecticide, its susceptibility to leaching has so far precluded its use as an exterior grade preservative.

The results detailed in Table 4 show that in terms of preservative active element [a.e.] leached both CuLin2 and CuLin2 +cypermethrin perform exceedingly well for both cold and hot water [soxhlet] leaching. The results for CuLin2 a.e. leached [i.e. copper] also compare extremely favorably with the results obtained for copper-chrome-arsenic preservative [CCA].

Most importantly, CuLin2 performed much better than its potential low toxicity labelled counterparts copper and zinc naphthenate. This result is of significant commercial importance in that it gives CuLin2 a distinct advantage, in terms of desirability, for use under exterior service conditions where resistance is an important performance requirement.

EXAMPLE 5

Thermal Stability tests

Similar specimens [20×20×10 mm] used for the leaching tests were also used for the testing of the thermal stability of CuLin2 as a preservative in comparison with other compounds treated to different retention levels. The pieces were placed in an oven at 70° C. for five days under standard atmospheric conditions. The temperature of 70° C. was chosen to be representative of the maximum temperature reached in summer under roof conditions in South Africa. The mass difference calculated of the treated timber before and after the test are shown in Table 5.

TABLE 5

THERMAL STABILITY TEST RESULTS [70° C.]

| Treatment | Total average retention (Kg a.i./m$^3$)* | Total preservative mixture thermal loss at 70° C. % |
|---|---|---|
| CuLin2 | 10.61 | 0.41 |
|  | 14.25 | 0.85 |
|  | 20.73 | 0.45 |
| CuLin2 + | 7.72 | 0.42 |
| Cypermethrin | 9.83 | 0.43 |
|  | 15.07 | 0.00 |
| Cypermethrin | 0.11 | 0.00 |
|  | 0.15 | 0.45 |
|  | 0.21 | 0.45 |
| CCA | 4.39 | 0.41 |
|  | 9.13 | 1.75 |
|  | 14.80 | 0.89 |
| PCP | 4.25 | 0.44 |
|  | 8.53 | 0.00 |
|  | 13.16 | 0.83 |
| Creosote | 30.78 | 0.83 |
|  | 68.95 | 0.43 |
|  | 102.07 | 2.09 |
| Copper | 1.19* | 0.00 |
| naphthenate | 1.54* | 0.96 |
|  | 1.97* | — |
| Zinc naphthenate | 1.11* | 0.78 |
|  | 1.61* | 1.70 |
|  | 2.15* | 3.00 |
| Controls | 0.00 | 0.00 |

*Kg a.e. Cu or Zn/m$^3$; a.i. = active ingredient

Discussion

The thermal stability test which was aimed at establishing the preservative stability for timber roof truss treatments in hot climates demonstrated that CuLin2 was stable and indeed performed equally or better than CCA which is already extensively used for roof truss protection. However, it should be noted from the results in Table 2 that the loss of preservative from each of the preservatives tested was minimal.

EXAMPLE 6

Burn tests

A burn test method was developed during the development of fire retardants for mining timber [W. E. Conradie, A. Pizzi and M. C. Vogel, 1983] which has been adopted as a standard method by the South African Chamber of Mines. Ten Pinus patula blocks measuring 20×20×10 mm were treated with the preservatives mentioned above, to the aimed retentions. After conditioning to ±10% M C and weighing, each specimen was subjected to the burn test which measures under standardized and very severe conditions the ignition time, its mass loss percentage while burning during a standardized time at 600° C. and the final temperature after burning. An afterglow rating from 0 to 3 is also given to each block and the time mass loss of the treated timber due to afterglow is measured. The results obtained are shown in Table 6.

TABLE 6

BURN TEST RESULTS

| Treatment | Average preservative retention (Kg/a.i. m$^3$) | Average ignition time (sec) | Average final temp. (°C.) | Average mass loss after burning (%) | Average afterglow rating | Average mass loss after glowing (%) | Average total mass loss (%) |
|---|---|---|---|---|---|---|---|
| CuLin2 | 9.65 | 1.8 | 642.1 | 38.2 | 1.1 | 4.50 | 42.70 |
|  | 14.76 | 1.7 | 647.9 | 40.3 | 1.1 | 7.07 | 47.37 |
|  | 20.23 | 1.9 | 639.6 | 40.8 | 1.5 | 6.85 | 47.65 |
| CuLin 2 + | 7.37 | 1.6 | 645.1 | 40.3 | 1.3 | 6.36 | 46.66 |
| Cypermethrin | 10.10 | 2.1 | 645.2 | 38.3 | 1.2 | 7.71 | 46.01 |
|  | 14.69 | 2.1 | 639.6 | 35.3 | 0.9 | 5.49 | 40.79 |
| Cypermethrin | 0.12 | 2.0 | 637.0 | 39.8 | 0.0 | — | 39.8 |
|  | 0.17 | 1.8 | 664.3 | 39.1 | 0.0 | — | 39.1 |
|  | 0.19 | 1.8 | 647.3 | 37.5 | 0.0 | — | 37.5 |
| CCA Type C | 4.50 | 2.2 | 632.0 | 38.9 | 0.3 | 1.31 | 40.21 |
| Salt | 9.20 | 4.5 | 649.4 | 40.6 | 0.4 | 2.85 | 43.45 |
|  | 14.85 | 7.0 | 629.5 | 41.1 | 0.5 | 6.88 | 47.87 |
| PCP | 4.38 | 2.3 | 647.2 | 40.0 | 0.0 | — | 40.0 |
|  | 8.84 | 2.6 | 644.4 | 35.4 | 0.0 | — | 35. |
|  | 13.28 | 2.8 | 648.3 | 37.4 | 0.0 | — | 37.4 |
| Creosote | 32.05 | 3.4 | 647.3 | 38.8 | 0.0 | — | 38.8 |
|  | 66.58 | 2.9 | 654.5 | 40.2 | 0.0 | — | 40.2 |
|  | 99.87 | 3.0 | 655.8 | 41.3 | 0.0 | — | 41.3 |
| Copper | 1.49* | 2.2 | 647.2 | 39.8 | 0.7 | 4.52 | 44.32 |
| naphthenate | 1.52* | 2.5 | 644.4 | 40.3 | 0.8 | 3.58 | 43.88 |
|  | 2.08* | 2.3 | 648.3 | 38.1 | 1.0 | 5.24 | 43.34 |
| Zinc | 0.90* | 3.6 | 642.0 | 38.25 | 0.0 | — | 38.25 |
| naphthenate | 1.41* | 3.5 | 637.0 | 37.07 | 0.0 | — | 33.91 |
| Untreated controls | 0.00 | 1.71 | 647.8 | 40.74 | 1.2 | 0.35 | 41.09 |

*Kg a.e. Cu or Zn/m$^3$; a.i. = active ingredient

Discussion

The results from the burn tests give some reason for concern in that CuLin2 treatments exhibited the highest average afterglow rating and relatively high level of mass loss after glowing when compared with the other preservatives tested. However, it must be borne in mind that these values did not exceed that encountered in the untreated controls.

The high afterglow rating and mass loss after glowing of CCA-treated samples were anticipated in that afterglow problems in CCA-treated timber is well recognized and is thought to be a function of the chromium component in CCA, which acts as a glow promoter. However, the fact that only the copper bearing preservatives, i.e. copper linoleate, CCA and copper naphthenate exhibited afterglow problems is interesting and the reasons for this obviously requires further elucidation. The fact that zinc naphthenate did not produce afterglow would seem to preclude the fatty acid component of both copper linoleate and copper naphthenate as having an influence and therefore highlights the potential influence of the copper as a factor and this will be investigated further.

In terms of overall mass loss as a result of burning, CCA, copper linoleate and copper naphthenate all performed comparably to the untreated controls and thus exhibited no degree of fire retardancy. In contrast, zinc naphthenate performed better, on average, than the untreated controls and as such did exhibit some degree of fire retardancy.

EXAMPLE 7

Corrosive properties of CuLin2

Preservative compositions of CuLin2 were made up respectively in water and xylene to contain 0.448% Cu active element on a mass to mass basis. The xylene solution was designated CuLin (OS) to signify the organic solvent and the aqueous formulation was designated CuLin (EC) to signify the emulsifiable concentrate of the formulation.

Comparative preservative formulations of copper chrome arsenate [CCA] and copper sulfate [$CuSO_4$] were also made up to contain 0.448% copper active element.

Experimental 10 mild steel and 10 brass strips [150×25×1 mm] per preservative solution were subjected to an immersion test to determine the corrosion effect on metals in contact with treatment solutions.

Five strips from each solution were removed after a 2 month and a 3 month exposure period, respectively and the mass losses were determined and expressed as $mg/cm^2$ as well as a percentage of original mass.

The results are set out in Table 7 below.

TABLE 7

| CORROSION TEST RESULTS [SOLUTION IMMERSION] | | | | | |
|---|---|---|---|---|---|
| | | MILD STEEL - MASS LOSS | | | |
| | Cu, | 2 MONTHS | | 3 MONTHS | |
| SOLUTION | % (m/m) | mg/cm² | % | mg/cm² | % |
| 5.0% (m/m) CCA | 0.448 | 1.39 | 0.38 | 2.03 | 0.56 |
| 1.76% (m/m) CuSO₄.5H₂O | 0.448 | 48.62 | 13.42 | 50.75 | 13.95 |
| 6.11% (m/m) CuLin (OS) | 0.448 | 0.09 | 0.02 | 0.08 | 0.02 |
| 3.85% (m/m) CuLin (EC) | 0.448 | 0.65 | 0.18 | 1.35 | 0.37 |
| H₂O control | — | 2.66 | 0.73 | 4.71 | 1.29 |
| | | BRASS - MASS LOSS | | | |
| | Cu, | 2 MONTHS | | 3 MONTHS | |
| SOLUTION | % (m/m) | mg/cm² | % | mg/cm² | % |
| 5.0% (m/m) CCA | 0.448 | 0.85 | 0.21 | 1.29 | 0.32 |
| 1.76% (m/m) CuSO₄.5H₂O | 0.448 | 6.65 | 1.66 | 8.27 | 2.06 |
| 6.11% (m/m) CuLin (OS) | 0.448 | 0.27 | 0.07 | 0.51 | 0.13 |

TABLE 7-continued

| CORROSION TEST RESULTS [SOLUTION IMMERSION] | | | | | |
|---|---|---|---|---|---|
| 3.85% (m/m) CuLin (EC) | 0.448 | 0.45 | 0.11 | 0.66 | 0.16 |
| H₂O control | — | 0.19 | 0.05 | 0.21 | 0.05 |

Discussion

It will be seen that the CuLin formulations have a very low corrosive nature to mild steel and brass when compared to even CCA.

In comparison with the water control, all the solutions tested except for copper sulphate showed a lower degree of corrosion on mild steel, CuLin2 (OS), showing virtually no corrosive effect. CuLin EC also shows a very low degree of corrosion and is comparable to CCA.

Regarding the corrosiveness on brass CuLin2 (OS) also showed the lowest effect, followed by the CuLin EC. Thus both formulations performed better than CCA. It is therefore apparent that in both CuLin formulations tested the highly corrosive nature of copper is susppressed.

EXAMPLE 8

Biological Performance of CuLin Emulsifiable Concentrate [EC] Preparation on Termites and Fungi A. Preparation of Preservative Compositions and Controls

[i] CuLin EC

An emulsifiable concentrate of the CuLin2 material was prepared and coded CuLin EC.

CuLin EC was formulated as follows:

| Ingredients | Quantities in g/l |
|---|---|
| CuLin2 Technical [7.1% m/m] | 668.0 |
| Tensio fix B7438 | 60.0 |
| Tensio fix B7453 | 90.0 |
| Xylene | 112.0 |
| The Cu-content = 5.05% m/m | |
| = 4.74% m/v | |
| = 47.4 g/l | |

The technical CuLin2 [7.1% m/m] is first dissolved in xylene to render it fluid. Then the Tensio fix B7438 and B7453 emulsifiers [a pair of cationic and anionic emulsifiers] are added.

The formulation is then made up to 1 liter with xylene. The theoretical density at room temperature and pressure is 0.940 kg/liter or 940 kg–1000 liters.

The CuLin EC in this form was stable and simple to apply and therefore no other modifications to the mixture were made. The stability of the CuLin EC was tested by leaving it for a few months, and the results showed that CuLin EC has a very good shelf life.

[ii] CuLin EC +Cypermethrin

In the manner described above in Example 1 a combination product containing CuLin EC and cypermethrin EC was prepared and water was used as the carrier system.

Comparative Formulations and Controls

In addition to the test formulations referred to above other preservative formulations described in Example 3 were used in accordance with the manufacturer's recommendations.

A test program, similar to the program described in Examples 1, 2 and 3 above commencing during December 1990 [termite tests] and January 1991 [fungal tests] was conducted and the same evaluation system was followed. In this program 10 replicates were used for each formulation. Five replicates were aged and five were unaged for each test.

The results are set out in Table 8.

TABLE 8

BIOLOGICAL PERFORMANCE OF COPPER LINOLEATE EMULSIFIABLE CONCENTRATE IN COMPARISON WITH OTHER WOOD PRESERVATIVES AGAINST TERMITES AND FUNGI [CuLin2: EC FORMULATION] [PLACED TERMITES: 13/12/1990; FUNGI: 05/01/1991]

| | | Grade of attach (%) after x months exposure | | | | | | | | | | |
|---|---|---|---|---|---|---|---|---|---|---|---|---|
| | | 3 Months | | | | 5 Months | | | | 7 Months | | | |
| | Retention | Termites | | Fungi | | Termites | | Fungi | | Termites | | Fungi | |
| Preservatives | (kg a.e./m³)* | Aged | Un-aged | Aged | Un-aged | Aged | Un-aged | Aged | Un-aged | Aged | Un-aged | Aged | Un-aged |
| CuLin EC | 1.0 | 0 | 0 | 0 | 5.2 | 2.4 | 0 | 4.5 | 8.8 | 2.4 | 0 | 8.0 | 11.6 |
| | 1.5 | 0 | 0 | 0 | 1.5 | 0 | 0 | 6.0 | 6.0 | 0 | 0 | 9.5 | 6.0 |
| | 2.0 | 0 | 0 | 0 | 1.5 | 0 | 0 | 6.0 | 6.0 | 0 | 0 | 6.0 | 6.0 |
| CuLin EC + | 0.25 + 0.025 | 0 | 0 | 2.0 | 6.5 | 0 | 0 | 13.3 | 9.5 | 0 | 0 | 53.3 | 14.5 |
| Cypermethrin | 0.25 + 0.125 | 0 | 0 | 1.5 | 4.0 | 0 | 0 | 4.5 | 7.6 | 0 | 0 | 4.5 | 30.4 |
| EC** | 0.5 + 0.05 | 0 | 0 | 1.2 | 1.2 | 0 | 0 | 4.0 | 2.4 | 0 | 0 | 6.0 | 2.4 |
| | 0.5 + 0.125 | 0 | 0 | 2.0 | 1.2 | 0 | 0 | 4.0 | 6.4 | 0 | 0 | 4.0 | 10.4 |
| | 0.75 + 0.075 | 0 | 0 | 2.4 | 0 | 1.2 | 0 | 4.0 | 6.0 | 1.2 | 0 | 4.8 | 6.0 |
| | 1.0 + 0.1 | 0 | 0 | 0 | 1.5 | 0 | 0 | 4.5 | 3.0 | 0 | 0 | 15.0 | 3.0 |
| | 1.5 + 0.15 | 0 | 0 | 4.0 | 1.2 | 0 | 0 | 7.6 | 6.0 | 0 | 0 | 7.6 | 6.0 |
| CuLin2 | 1.0 | 0 | 0 | 7.6 | 5.2 | 0 | 1.2 | 8.8 | 7.6 | 0 | 0 | 8.8 | 7.6 |
| | 1.5 | 0 | 0 | 2.4 | 0 | 0 | 0 | 6.0 | 3.6 | 0 | 0 | 8.8 | 3.6 |
| | 2.0 | 0 | 0 | 1.2 | 2.4 | 0 | 0 | 3.6 | 3.6 | 0 | 0 | 4.8 | 6.4 |
| Cypermethrin** | 0.1 | 0 | 0 | 4.0 | 8.0 | 0 | 0 | 12.8 | 16.8 | 0 | 0 | 12.8 | 24.8 |
| (OS) | 0.15 | 0 | 0 | 6.5 | 25.0 | 0 | 0 | 14.4 | 28.0 | 0 | 0 | 42.4 | 33.0 |
| | 0.20 | 0 | 0 | 25.0 | 0 | 0 | 0 | 33.0 | 6.0 | 0 | 0 | 38.4 | 6.0 |
| CuLin2 + | 0.75 + 0.075 | 0 | 0 | 0 | 0 | 0 | 0 | 6.0 | 6.0 | 0 | 0 | 6.0 | 43.0 |
| Cypermethrin** | 1.0 + 0.1 | 0 | 0 | 0 | 1.2 | 0 | 0 | 6.0 | 8.8 | 0 | 0 | 15.6 | 15.6 |
| (OS) | 1.5 + 0.15 | 0 | 0 | 0 | 1.2 | 0 | 0 | 4.8 | 3.8 | 0 | 0 | 4.8 | 11.6 |
| CCA Type C | 0.45 | 0 | 0 | 0 | 0 | 1.2 | 1.2 | 6.0 | 6.0 | 1.2 | 1.2 | 24.8 | 12.8 |
| Salt | 0.90 | 0 | 0 | 1.2 | 0 | 0 | 0 | 6.0 | 4.8 | 0 | 0 | 6.0 | 6.0 |
| | 1.35 | 0 | 0 | 0 | 1.2 | 0 | 0 | 6.0 | 6.0 | 0 | 0 | 6.0 | 6.0 |
| PCP** (OS) | 5 | 1.2 | 40.0 | 1.2 | 1.2 | 1.2 | 4.0 | 8.8 | 6.0 | 1.2 | 4.0 | 15.6 | 19.6 |
| | 10 | 0 | 0 | 1.2 | 0 | 0 | 0 | 6.0 | 4.8 | 0 | 0 | 12.8 | 11.6 |
| | 15 | 0 | 0 | 0 | 1.2 | 0 | 0 | 6.0 | 6.0 | 0 | 0 | 6.0 | 6.0 |
| Creosote** | 33 | 0 | 0 | 2.4 | 3.6 | 0 | 1.2 | 4.8 | 8.8 | 0 | 1.2 | 4.8 | 15.6 |
| | 67 | 0 | 0 | 4.0 | 0 | 0 | 0 | 7.6 | 3.6 | 0 | 0 | 7.6 | 4.8 |
| | 100 | 0 | 0 | 1.2 | 0 | 0 | 0 | 6.0 | 6.0 | 0 | 0 | 8.8 | 6.0 |
| Cu naphthenate | 1.0 | 1.2 | 4.0 | 0 | 0 | 1.2 | 4.0 | 2.4 | 6.0 | 1.2 | 4.0 | 3.6 | 24.8 |
| (OS) | 1.5 | 0 | 0 | 1.2 | 3.6 | 0 | 1.2 | 6.0 | 6.0 | 0 | 1.2 | 6.0 | 6.0 |
| | 2.0 | 0 | 0 | 3.6 | 3.6 | 0 | 0 | 6.0 | 6.0 | 0 | 0 | 6.0 | 6.0 |
| Zn naphthenate | 1.0 | 40.0 | 32.0 | 5.2 | 4.0 | 40.0 | 36.0 | 15.6 | 11.6 | 40.0 | 36.0 | 46.4 | 23.6 |
| (OS) | 1.5 | 64.0 | 20.0 | 8.0 | 0 | 64.0 | 22.4 | 23.6 | 4.8 | 64.0 | 22.4 | 31.6 | 34.4 |
| | 2.0 | 32.0 | 16.0 | 0 | 0 | 53.2 | 17.2 | 6.0 | 6.0 | 53.2 | 17.2 | 6.0 | 24.8 |
| Untreated Controls | — | 72.0 | 92.0 | 60.0 | 52.0 | 82.0 | 92.0 | 62.4 | 57.2 | 82.0 | 94.0 | 62.4 | 79.2 |
| White Spirits | — | — | 90.0 | — | 44.0 | — | 90.0 | — | 47.0 | — | 90.00 | — | 50.4 |
| Xylene | — | — | 72.0 | — | 44.0 | — | 72.0 | — | 49.8 | — | 72.0 | — | 67.8 |
| Toluene | — | — | 56.0 | — | 43.2 | — | 58.0 | — | 47.8 | — | 58.0 | — | 55.8 |

*a.e. = active element [Cu or Zn]
**retention based on total product

It can be seen from Table 8 that the water based CuLin EC formulation is performing well [i.e. having minimal degrade] against both termites and fungi in comparison to current commercial formulations [e.g. CCA] and CuLin (OS) after a 7 month exposure period. In addition the water based CuLin EC plus Cypermethrin EC formulation is also performing well against both termites and fungi in comparison to commercial formulations [e.g. CCA] after a 7 month exposure period and is indeed outperforming its organic solvent equivalent [CuLin +Cypermethrin (OS)] in relation to fungal attack.

It will be appreciated that many variations of the invention may be devised without thereby departing from the spirit of the invention which relates to the treatment composition as disclosed herein, the method of treatment described and to wooden articles treated by the composition.

We claim:

1. A wood preservative composition comprising a mixture of two or more metallic soaps of long chain unsaturated fatty acids, which soaps have a metallic component selected from the group consisting of copper, zinc, chromium, iron, antimony, tin, cobalt, nickel, arsenic, boron, lead, magnesium, potassium and sodium, and a fatty acid component selected from two or more of the group consisting of oleic acid, linoleic acid, and linolenic acid, the composition being such that the ratio by mass of metallic soap of oleic acid:metallic soap of linoleic acid:metallic soap of linolenic acid is about 20–29:15–70:0–47.

2. A preservative composition as claimed in claim 1 wherein the metallic soap mixture has an iodine value of between 125 and 180.

3. A preservative composition as claimed in claim 2 wherein the composition additionally comprises saturated fatty acid metallic soaps derived from an acid selected from the group consisting of stearic acid and palmitic acid in a quantity constituting between 1.0 and 6.5 parts per mass for soap derived from stearic acid and between 5 and 11.5 parts by mass for the soaps derived from palmitic acid.

4. A preservative composition as claimed in claim 3 wherein the mass ratio of stearic acid soap:oleic acid soap:linoleic acid soap:linolenic acid soap:palmitic acid soap is about 1.0–6.5:24.5–28.6:49.8–70.0:0–0.4:5.0–11.5.

5. A composition as claimed in claim 4 wherein the ratio by mass of stearic acid soap:oleic acid soap:linoleic acid soap:linolenic acid soap:palmitic acid soap is about 4.8:26.6:54.8:0.1:8.5.

6. A preservative composition as claimed in claim 1 wherein the metallic component of the metal soaps is copper [$Cu++$].

7. A preservative composition as claimed in claim 1 wherein the wood preservative composition further includes an insecticide, fungicide mixture of insecticide and fungicide.

8. A preservative composition as claimed in claim 7 containing an insecticide, wherein the insecticide is a synthetic pyrethroid.

9. A preservative composition as claimed in claim 1 further comprising a carrier medium comprising xylene, wherein the composition contains a copper content of at least 5% by mass in xylene.

10. A preservative composition as claimed in claim 1 wherein the composition is modified to render it a water dispersible formulation of an emulsifiable concentrate or a microemulsion concentrate by using one or more appropriate surface active agents.

* * * * *